(12) United States Patent
Eckert

(10) Patent No.: US 7,288,574 B2
(45) Date of Patent: Oct. 30, 2007

(54) TWO-PHASE OXYGENATED SOLUTION AND METHOD OF USE

(76) Inventor: C. Edward Eckert, 260 Lynn Ann Dr., New Kensington, PA (US) 15068

( * ) Notice: Subject to any disclaimer, the term of this patent is extended or adjusted under 35 U.S.C. 154(b) by 77 days.

(21) Appl. No.: 10/197,787

(22) Filed: Jul. 18, 2002

(65) Prior Publication Data
US 2003/0021751 A1 Jan. 30, 2003

Related U.S. Application Data

(60) Provisional application No. 60/306,309, filed on Jul. 18, 2001.

(51) Int. Cl.
| | |
|---|---|
| B01J 13/00 | (2006.01) |
| B01F 3/04 | (2006.01) |
| A61K 8/22 | (2006.01) |
| A01N 25/04 | (2006.01) |
| A01N 25/16 | (2006.01) |

(52) U.S. Cl. .................. 516/10; 516/99; 516/110; 514/771; 514/944; 514/949; 424/613

(58) Field of Classification Search .......... 516/10, 516/99, 110; 424/613; 514/771, 944, 949
See application file for complete search history.

(56) References Cited
U.S. PATENT DOCUMENTS 2,836,497 A * 5/1958 Levin .................. 426/116
3,937,283 A * 2/1976 Blauer et al. .......... 166/307

(Continued)

OTHER PUBLICATIONS

On the www, Schlumberger, Bingham plastic model, Schlumberger at: http://www.glossary.oilfield.slb.com/Display.cfm?Term=Bingham%20plastic%20model , 4 pages, printed Oct. 2004.*

(Continued)

Primary Examiner—Daniel S. Metzmaier
(74) Attorney, Agent, or Firm—Patrick J. Hagan, Esq.; Dann, Dorfman, Herrell and Skillman, P.C.

(57) ABSTRACT

A two-phase mixture is provided having a dissolved gas and a suspension of bubbles in a liquid. Methods for making, maintaining, and using the two-phase mixture are also provided. The gas molecules may be introduced into the liquid at a high velocity under elevated pressure to form a supersaturated solution that retains the dissolved gas concentration in solution when the solution is exposed to ambient conditions. The mixture may be used in a number of applications where high concentrations of gas must be retained in solution during prolonged exposure to ambient conditions. An example of use is the treatment of wounds to non-surgically remove dead, devitalized, contaminated and foreign matter from tissue cells. The mixture may be combined with a plastic to encapsulate the suspension of bubbles to minimize liberation of the gas bubbles from the mixture.

6 Claims, 4 Drawing Sheets

U.S. PATENT DOCUMENTS

| | | | |
|---|---|---|---|
| 4,049,491 A * | 9/1977 | Brandon et al. | 162/101 |
| 4,366,169 A | 12/1982 | White | 417/250 |
| 4,388,485 A * | 6/1983 | Zeidler et al. | 174/23 C |
| 4,685,519 A * | 8/1987 | Stowe et al. | 166/278 |
| 5,463,176 A | 10/1995 | Eckert | 210/622 |
| 5,547,347 A | 8/1996 | Sethna et al. | 514/755 |
| 5,688,490 A * | 11/1997 | Tournier et al. | 424/9.52 |

OTHER PUBLICATIONS

Khan et al, "Foam Rheology: III. Measurement of Shear Flow Properties", J. Rheology, Jan. 1988, vol. 32, Issue 1, pp. 69-92.*

Colie, M.M. "Adjunctive Hyperbaric Oxygen Treatment of Severe Electrical Injuries: A Comparative Study in Humans", Annals of Burns and Fire Disasters Vol. XIII—n.4, Dec. 2000, Internet URL http://www.medbc.com (retrieved May 31, 2001).

Singer, Neal, Sandia National Laboratories, "Sandia Research Agreement with Numotech to Help Create Home-Use Oxygen-Healing Facility", Jun. 19, 1998, Internet URL http://www.sandia.gov (retrieved May 31, 2001).

Youn, Brian A., M.D., "Oxygen and Its Role in Woundk Healing", Environmental Tectonics Corporation, Internet URL http://www.etcusa.com (retrieved May 31, 2001).

* cited by examiner

FIG. 4 ical and
energetically inefficient to operate at exceptionally small
orifice diameters. This process also has an absolute limit as
a gas velocity of Mach one is approached within the pore.
Because a pore lacks the convergent/divergent geometry
required to achieve supersonic flow, increasing pressure
beyond the critical pressure will not result in a further
reduction of bubble size.

TWO-PHASE OXYGENATED SOLUTION AND METHOD OF USE

PRIORITY CLAIM

This application claims priority to U.S. Provisional Application No. 60/306,309, filed Jul. 18, 2001, which is hereby incorporated herein by reference.

FIELD OF THE INVENTION

The present invention relates to solutions of dissolved gas, and more specifically, to multi-phase mixtures containing a solution of gas and a dispersion of gas micro-bubbles in colloidal suspension.

BACKGROUND OF THE INVENTION

Oxygenated solutions are used in a variety of applications where elevated dissolved oxygen content is desired. In the medical community, it is generally known that the effect of oxygen on living tissue can be characterized by three regimes, namely, metabolic enhancement (growth accelerator), metabolic inhibition (growth arrest), and toxicity. In the former regime, oxygenated solutions can be used to accelerate the healing and regeneration rate of damaged tissue. Such wounds include cuts, lacerations, sores and burns on the face, arms, legs, torso and roof of the mouth. When wounds begin to heal, fibroblastic cells divide and spread throughout the wound area. The fibroblastic cells produce collagen, an important protein that facilitates healing. Supplying sufficient quantities of oxygen to the wound area significantly enhances fibroblast proliferation. In particular, the fibroblastic cells use amino acids hydroxylated with oxygen to synthesize collagen chains. In addition to treating wounds, oxygen is frequently used in topical applications for cleaning and revitalizing skin. In facial cleansing, dissolved oxygen assists in exfoliating dead skin particles from the skin surface. Dissolved oxygen has also been used to remove toxins, particulates and other occlusions in skin pores. In addition, oxygen has been used to revitalize skin cells by joining with protein molecules to nourish the cells and produce collagen.

The amount of oxygen initially dissolved into solution is largely dependent on the method used to dissolve the oxygen gas into solution. One common method for oxygenating water is the coarse bubble aeration process, which is a subset of aeration methods known categorically as air diffusion. Pressurized air or oxygen gas is introduced through a submerged pipe having small holes or orifices into a container of water. Gas pressure is sufficient to overcome the hydrostatic head pressure, and also sustains pressure losses during passage through the small gas orifices. As a result, bubble aeration occurs at relatively low pressures; this pressure being predominantly a function of tube immersion depth.

Since all interphase interfaces have a characteristic surface energy, the creation of interfacial (surface) area is an energetic process. As a gas passes through an orifice, for example, pressure energy is converted to kinetic energy, which consequently satisfies the energetic requirements of the system for the production of surface area. Area and velocity are inversely proportional; hence, as the orifice diameter decreases, the corresponding pressure drop and gas velocity increase, and more surface area is generated. Smaller bubbles result. This process has a limiting condition, however, in that the amount of heat (as irreversible work) that is produced is inversely proportional to the square of orifice diameter. It therefore becomes impracti Since oxygen therefore is introduced into solution at relatively low pressures in the bubble aeration process, the oxygen bubbles are relatively large. As a result, the aggregate bubble surface area for a dispersion of bubbles produced by bubble aeration is relatively small. The limited surface area produced by bubble aeration limits the concentration of gas that can be dissolved into solution. Oxygen dissolution is a function of the interfacial contact area between gas bubbles and the surrounding medium, and bulk fluid transport (mixing) in the liquid phase. In particular, the rate of oxygen dissolution is directly proportional to the surface area of the bubbles. A dispersion of very small bubbles, e.g. bubbles having diameters in the order of 50 microns, will have a much larger total surface area than a dispersion of large bubbles occupying the same volume. Consequently, the rate of oxygen dissolution in bubbling aeration is limited by the size of the bubbles introduced into the solvent. Fluid mixing is also very limited in bubbling aeration because the only energy source available for agitation is the isothermal expansion energy of oxygen as it rises in the solution.

Oxygen dissolution in bubbling aeration is also limited by ambient pressure conditions above the solution. If the solution being aerated is exposed to atmospheric conditions, the dissolved oxygen concentration will be limited to the solubility limit of oxygen (at its partial pressure in air of 0.21 atm) under such conditions. The desirability of bubbling aeration is further hampered by equipment and energy requirements. Large blower units are used to force the gas bubbles into the carrying liquid. These blowers generate high-energy costs and often require special soundproof installations or other engineering costs.

Hydrogen peroxide is another popular source of oxygen used in topical applications and baths. Oxygen is easily derived from hydrogen peroxide, or $H_2O_2$, because an $H_2O_2$ molecule readily dissociates into water ($H_2O$) and an oxygen free-radical. The decomposition of $H_2O_2$ into water and oxygen free-radicals creates an enriched solution that facilitates dermal contact with oxygen. Hydrogen peroxide is distributed in various grades and concentrations that are specific to certain applications. Solutions of 3% and 6% hydrogen peroxide are commonly sold to consumers who use the solutions to disinfect cuts and clean skin areas. Solutions of 35% hydrogen peroxide are frequently added to spas and hot tubs to disinfect the water. Skin therapists use solutions of 35% hydrogen peroxide in oxygen baths to improve tissue regeneration and remove toxins from the dermis. Some topical creams contain stabilized forms of hydrogen peroxide intended to prevent free-radical formation and infections in skin.

Despite being a significant source of oxygen, hydrogen peroxide has been the subject of significant controversy when used in skin treatment applications. Some authorities claim that hydrogen peroxide is cytotoxic to human fibroblasts, due to the presence of free-radical oxygen. As a result, some medical professionals recommend additional dilution of hydrogen peroxide solutions to avoid their toxic effects on skin. Authorities also state that hydrogen peroxide reduces white blood cell activity. Still others have found that hydrogen peroxide slows wound healing by drying the wound, which destroys the exudate and leads to necrosis of skin tissue. Dry tissue also makes the wound area prone to bacterial growth and infection. As a result, hydrogen peroxide has drawn some questions as to its suitability for treating skin wounds and burns.

SUMMARY OF THE INVENTION

Based on the foregoing, an oxygenated mixture is provided having a dissolved molecular oxygen content well above the equilibrium limit at ambient conditions. The oxygenated mixture can supply a large amount of molecular oxygen in a medium that is not traumatic to skin tissue. Since the dissolution of oxygen into solution occurs under hyperbaric conditions, a large concentration of oxygen is dissolved into solution. The resulting solution can have a dissolved oxygen content as high as 200 mg/l. In one embodiment of the solution, an oxygen-enriched solution is accompanied by a dispersion of micro-bubbles held in suspension. In another embodiment, the oxygenated solution and micro-bubble dispersion are encapsulated in a Bingham Plastic.

A method for using the oxygenated solution in medical treatment is also provided. The method includes the step of filling a bath with oxygenated solution and a micro-bubble dispersion. Wounded areas of a patient, such as burned tissue, are submerged into the oxygenated solution and dispersion. The solution is allowed to enter tiny fissures or cavities in the wounded tissue. Some of the dissolved oxygen contacts the wounded tissue and aids in the regeneration of new tissue cells. As the solution is circulated in the tissue layers, the dissolved oxygen nucleates into fine micro-bubbles that attach to skin fragments. A volume change occurs upon nucleation of the oxygen bubbles. The dispersion of micro-bubbles and nucleating bubbles exfoliate damaged tissue layers and non-surgically remove dead, devitalized, contaminated and foreign matter from the tissue cells as the bubbles rise to the surface of the bath, further assisting in debridement and the regeneration of new tissue cells.

DESCRIPTION OF THE DRAWINGS

The foregoing summary as well as the following description will be better understood when read in conjunction with the figures, in which.

DETAILED DESCRIPTION OF THE INVENTION

Figure 1:
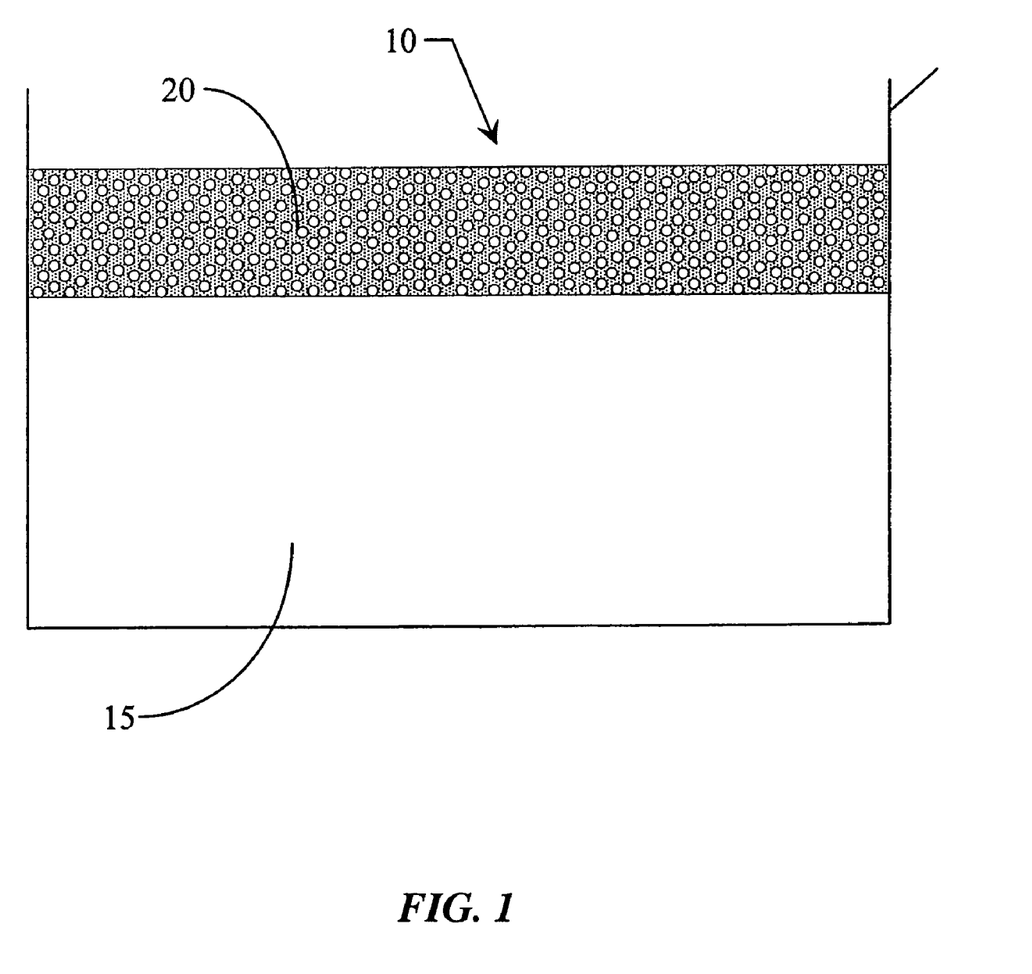
FIG. 1 is a cross sectional view of a two-phase mixture containing a gas enriched solution and micro-bubble dispersion in accordance with the present invention.

Referring to FIGS. 1-4 in general and FIG. 1 specifically, a two-phase mixture 10 containing a dissolved gas is illustrated. The mixture 10 contains a homogeneous solution 15 and a suspension or emulsion 20. The solution 15 contains a gas, such as oxygen, dissolved in a solvent, such as water. The suspension 20 is formed by a dispersion of micro-bubbles containing a gas, such as oxygen. For purposes of this description, the mixture 10 will be described as containing pure oxygen gas in water. However, it is intended that the mixture may contain other solute gases and solvents, as will be discussed further below.

FIG. 1 shows the two-phase mixture in a static condition, where the mixture is stored in a vessel 5. The micro-bubble dispersion 20 consists primarily of oxygen gas bubbles that have nucleated out of the solution 15. The micro-bubble suspension 20 has a lower density than the solution phase 15 and therefore forms a stratified layer on top of the solution. Although it is not clear from FIG. 1, the micro-bubble dispersion 20 typically has an occluded or cloudy appearance. This is caused by the scattering of visible light energy through the micro-bubble surfaces.

Referring again to FIG. 1, the homogeneous solution 15 will be described in further detail. The solubility limit of oxygen in water under equilibrium conditions with air ($p_{O2}$=0.21) at 77° F. is approximately 8.3 mg/l. When the two-phase mixture 10 is initially exposed to atmospheric conditions, the homogeneous solution 15 has a supersaturated oxygen content, i.e. above the solubility limit of oxygen in water under atmospheric conditions. Preferably, the homogeneous solution 15 has a dissolved oxygen concentration above 20 mg/l at 1 atm and 65° F. More preferably, the solution 15 has a dissolved oxygen concentration above 40 mg/l at 1 atm and 65° F. As a result, the oxygen concentration in the solution 15 is not stable when exposed to atmospheric conditions. Over time, exposure of the solution 15 to atmospheric conditions will cause some of the dissolved oxygen to be lost through ebullition. More specifically, over time, dissolved oxygen molecules will gradually nucleate out of solution 15 into gas bubbles. Depending on pressure and temperature conditions, the concentration of dissolved oxygen will decrease down to the equilibrium concentration over a period of several minutes.

The supersaturated oxygen content in solution 15 is preserved by limiting agitation and preventing flow conditions in the solution that can facilitate ebullition of oxygen gases. The high dissolved oxygen content is also maintained by storing the solution 15 in a manner that limits or prevents desorption of the gas. For instance, the solution may be stored and distributed in sealed screw top containers constructed of glass or alternative materials impervious to oxygen diffusion at these high oxygen concentrations.

If oxygenated water is stored in capped bottles, made of an oxygen impervious material, elevated oxygen concentrations can be preserved for extended periods. In an experiment, seven glass bottles were filled with oxygenated water, processed as previously described, and immediately capped. A polarographic probe was used to measure dissolved oxygen. The initial oxygen concentration was 64.2 mg/l, at a temperature of 17.6° C. Each bottle was uncapped for measurement of oxygen concentration at the intervals below:

| Initial | 6 hours | 1 day | 2 days | 3 days | 4 days |
|---------|---------|--------|--------|--------|--------|
| 64.2 mg/l | 65.7 mg/l | 63.5 mg/l | 67.5 mg/l | 58.5 mg/l | 55.4 mg/l |

It can be seen that over 86 percent of the original dissolved oxygen concentration was retained after 4 days. Such retention of oxygen in solution provides benefits in a number of applications. For example, a solution of oxygen dissolved in accordance with the above-described method may be used as an oxygen-enriched blood substitute.

As stated earlier, gas micro-bubbles that nucleate from solution, where the solution is a Newtonian fluid, such as water, rise to the surface and are released into the air above the solution. Gas bubbles rise in such fluids because a net body force exists that projects the bubbles upward. Since Newtonian fluids yield to these forces, the bubbles rise. These mechanics, which control bubble rise, are explained by Stokes Law, which will be examined later. In some applications, it is desirable to limit or substantially prevent bubbles from rising to the surface of the solution during storage and to maintain the micro-bubble dispersion indefinitely. In particular, it may be commercially desirable to market a product that contains visible oxygen bubbles that are held indefinitely in a suspension.

A supersaturated solution of oxygen in water is unstable at ambient pressure by definition. If, for example, the ambient temperature and pressure conditions establish an equilibrium oxygen concentration of 8 mg/l, and an oxygenated solution containing 40 mg/l is prepared at 5 atmospheres pressure, such a solution will have an oxygen concentration of 32 mg/l above the solubility limit. The oxygen-water system will attempt to reject oxygen by nucleating oxygen bubbles. Nucleation can be either a homogeneous or heterogeneous process, depending on changes in temperature, mechanical agitation, or the presence of suitable particles that can stimulate gas nucleation. Rapid pressure changes can provoke gas bubble nucleation, and in this invention, a reduction of pressure to ambient will typically result in the formation of micro-bubbles.

The micro-bubble dispersion 20 is characterized as having a very large surface area through which interfacial transport of oxygen occurs. Interfacial transport of oxygen through a large surface area aids in resupplying oxygen to solution when dissolved oxygen is taken up during chemical reactions. As a result, a large surface area in the micro-bubble dispersion is desirable.

The mixture 10 preferably contains micro-bubbles having an average bubble diameter of about 10-100 microns. Micro-bubbles within this size range provide a significantly larger surface area than a cluster of large bubbles containing the same volume of gas. The magnitude of this difference can be visualized by performing calculations for several bubble diameters at a constant volume of gas. The following calculations show the surface areas present for a single bubble, a plurality of one-inch diameter bubbles and a plurality of 50-micron diameter bubbles, wherein each calculation is based on one cubic foot of gas. The value, r, is the radius of a single bubble, $V_o$ is the volume of a single bubble, $A_o$ is the surface area of a single bubble, and A is the aggregate surface area for the bubble formation:

a. Single bubble:

$V_o=(4/3)\Pi r^3$; $r=(3V_o/4\Pi)^{1/3}$

Thus, when $V_o=1$ ft$^3$, r=0.6204 ft.
For a value of r=0.6204 ft, and if $A_o=4\Pi r^2$,
A=4.837 ft$^2$ and A=$A_o$ because a single bubble is being considered.

b. One inch bubbles:

r=0.5 inches=0.04167 ft.

$V_o=(4/3)\Pi r^3=(4/3)\Pi(0.04167$ ft$)^3=0.00030$ ft$^3$ per bubble

Bubble population (# bubbles)=(1 ft$^3$)/$V_o$=(1 ft$^3$/0.00030 ft$^3$)=3,300

$A=$(# bubbles)$\times A_o=3,300\times 4\Pi r^2=(3,300)4\Pi(0.04167$ ft$)^2$

A=71.99 ft$^2$ c. 50µ micro-bubbles:

$r=50\mu/2=25\mu=25\times 10^{-6}$ m=8.203$\times 10^{-5}$ ft.

$V_o=(4/3)\Pi r^3=(4/3)\Pi(8.203\times 10^{-5}$ ft$)^3=2.312\times 10^{-12}$ ft$^3$ per bubble bubbles=(1 ft$^3$)/$V_o$=(1 ft$^3$/2.312$\times 10^{-12}$ ft$^3$)=4.326$\times 10^{11}$ $A=$(# bubbles)$\times A_o=(4.326\times 10^{11})\times 4\Pi r^2=(4.326\times 10^{11})4\Pi(8.203\times 10^{-5})^2$ A=36,574 ft$^2$ Based on the foregoing calculations, the aggregate surface area for a dispersion of gas increases markedly as the radius of the bubbles decreases. Referring to calculations (b) and (c), a dispersion of 50-micron diameter bubbles containing one cubic foot of gas will have an aggregate surface area that is more than 500 times greater than a dispersion of one-inch bubbles containing the same volume of gas.

The micro-bubble suspension 20 is unstable, as the micro-bubbles tend to rise to the surface of the mixture and pass into the atmosphere over time. This movement is generally driven by buoyancy (body) forces. The mechanics of micro-bubble separation in a liquid can be analytically described by Stokes' Law for small bubble sizes:

$V=2gr^2(\delta_g-\delta_w)/9\eta$ where V is the terminal velocity of a bubble rising through the liquid, g is the acceleration of gravity, r is the radius of the bubble, $\delta_g$ is the density of the gas, $\delta_w$ is the density of the liquid, and $\eta$ is the Newtonian viscosity of the liquid. Based on the formula, the terminal velocity of a rising bubble is proportional to the square of the radius of the bubble. In other words, the net upward force that causes the bubble to rise (i.e. the buoyancy force less all drag forces on the bubble) increases dramatically as the size of the bubble increases. For this reason, it is advantageous to minimize the size of the bubble so that the rate of bubble rise is minimized. Even with micro-bubbles that have diameters of 50 microns, however, the bubbles will nevertheless rise to the surface, releasing oxygen gas from the dispersion.

One novel aspect of this invention involves the substitution of a Newtonian solvent with a Bingham Plastic. Such a material requires a finite yield stress to initiate movement, and is described by the following equation:

$\tau=+/-\tau_o+\eta_p\gamma$, where, $\tau$=shear stress, $\tau_o$=yield stress, $\eta_p$=plastic viscosity, and $\gamma$=strain rate. An important characteristic of a Bingham Plastic is that the yield stress, $\tau_o$, must be exceeded before flow, or strain, $\gamma$, can occur. Applied stress levels that are below the yield stress threshold will not result in movement of the fluid. A Bingham Plastic can be considered to have infinite viscosity and behave as a solid at stress levels below the yield stress. It can be seen from Stokes' Law, $$V=2gr^2(\delta_g-\delta_w)/9\eta,$$

that the limit of terminal velocity, V, is zero as the value for viscosity, $\eta$, approaches an infinite number. A Bingham Plastic will therefore result in bubble immobilization, provided that the magnitude of the buoyancy forces, $$4/3\Pi r^3(\delta_g-\delta_w)g,$$

exerts a stress level that falls below the yield stress for the Bingham Plastic. Bubble immobilization will provide stability of the micro-bubble suspension.

It has been discovered that the current invention can produce stable suspensions of micro-bubbles when a Bingham Plastic is used as the continuous, or solvent, phase. This is preferably accomplished by adding and mixing the ingredients to form a Bingham Plastic and an oxygenated liquid at elevated pressure, i.e.: prior to the formation of micro-bubbles. A high-pressure mixer, that is downstream of the oxygenation process, can be used for this purpose. Since the components are mixed prior to the solution being reduced to ambient pressure, micro-bubbles will not substantially form. Once the solution is reduced in pressure, micro-bubbles will form; however, these bubbles are immobilized by the previously formed Bingham Plastic.

A variety of Bingham Plastics provide a suitable solvent phase, including but not limited to formulations using clay based thickening agents, such as Optigel-SH® manufactured by Sud-Chemie, Inc., and formulations using polymeric based thickening agents, such as Carbopol® polymers manufactured by B. F. Goodrich Company. Where oxygen micro-bubbles are used, Optigel-SH® is a preferred solvent, because it contains an oxidation resistant substance. It has been found that oxygen micro-bubbles, immobilized in a Bingham Plastic using a polymeric thickening agent, can react with the polymer and slowly release heat as a result of the reaction. The extended contact time provided by bubble immobilization allows this oxidation reaction to occur.

Figure 2:
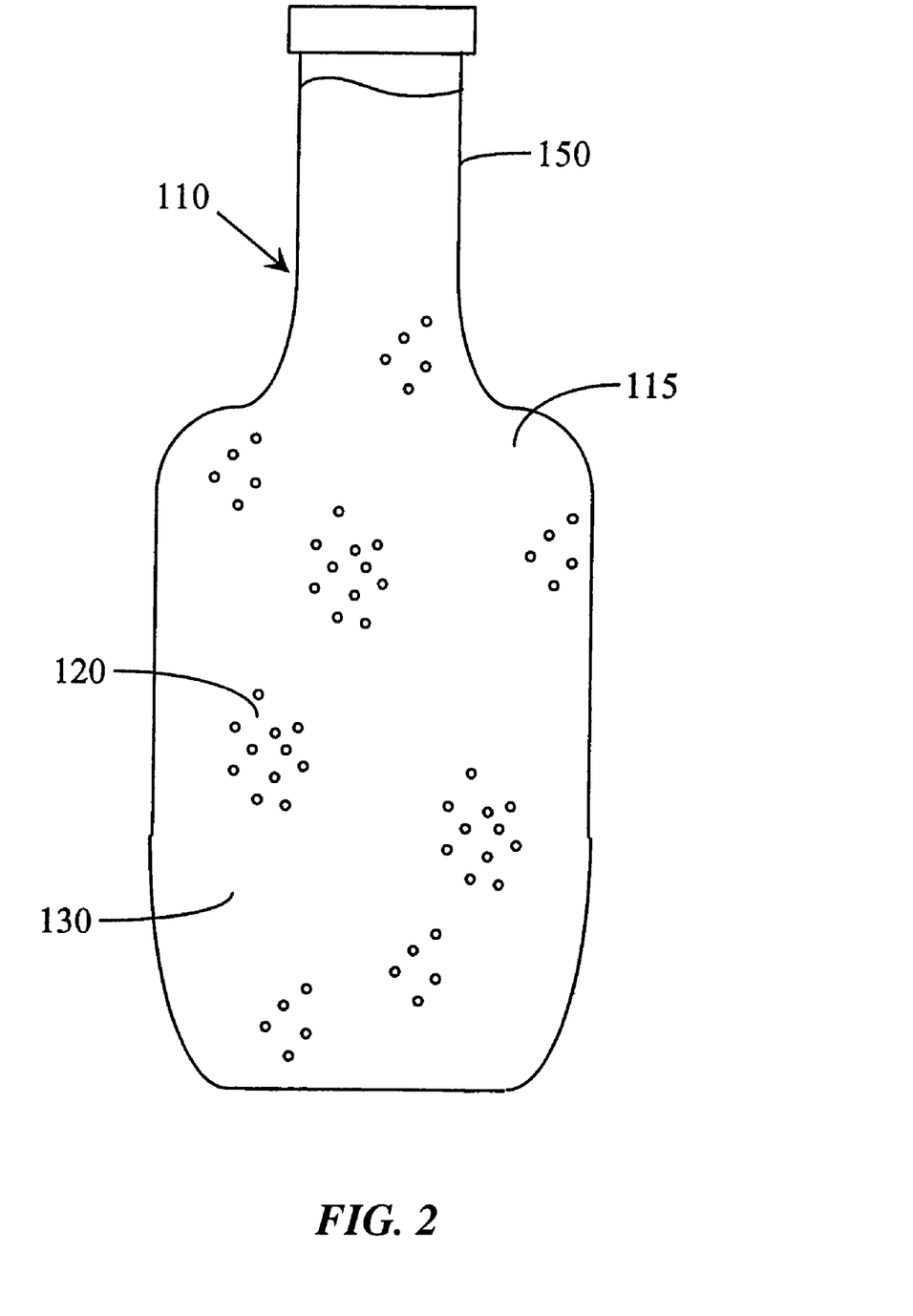
FIG. 2 is a frontal view of an alternate mixture in accordance with the present invention.

FIG. 2 illustrates a second embodiment of the present invention in which a Bingham Plastic 130 encapsulates a two-phase oxygenated mixture 110. The mixture 110 includes a homogeneous solution 115 of oxygen in water and a micro-bubble dispersion 120 contained in the Bingham Plastic 130. In FIG. 2, the mixture 110 is shown stored in a transparent bottle 150, which allows the oxygen gas micro-bubbles to be visible in the Bingham plastic 130 during storage. While the mixture 110 is shown stored in a bottle 150, the mixture is intended to be distributed in various types of containers, the choice of container being dependent on the type of product being marketed and the desired product configuration. The two-phase mixture 110 may be distributed with the Bingham Plastic 130 in a variety of products where there is a commercial interest in preserving the micro-bubble dispersion. For instance, the two-phase mixture and plastic may be marketed in shaving gels, hair gels, shampoos, ointments, lotions and other products.

The Bingham plastic 130 is characterized as having a finite yield stress. Fluid movement in a Bingham plastic 130 will not occur until the finite yield stress is exceeded. Once the yield stress has been exceeded, the stress may increase linearly with increasing shear rate. Buoyancy forces acting on the oxygen micro-bubbles 120 are insufficient to overcome the finite yield stress in the Bingham Plastic 130. Therefore, the Bingham Plastic 130 immobilizes the micro-bubbles 120 in the mixture for extended periods.

Figure 3:
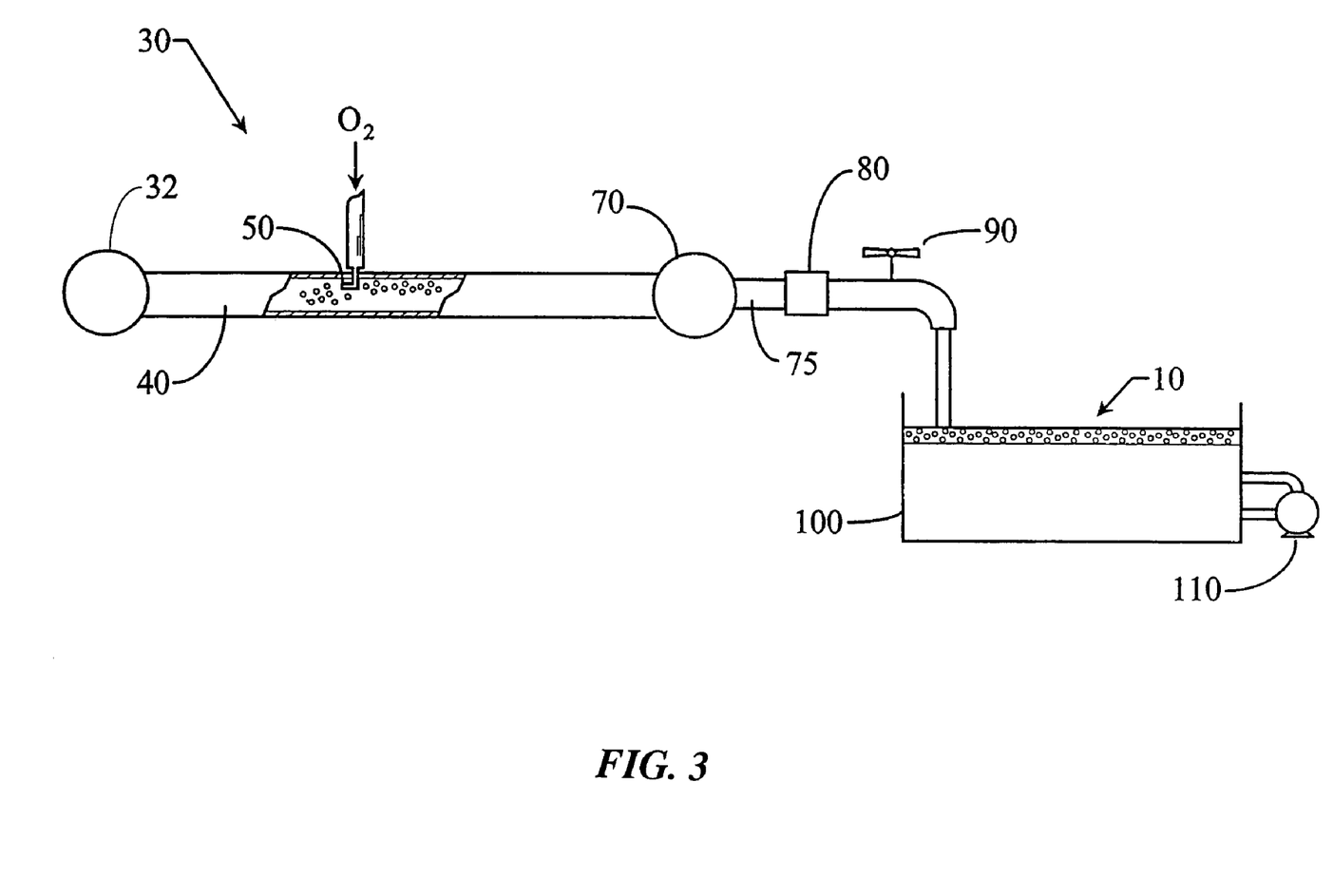
FIG. 3 is a flow chart showing steps of a method for generating and using a gas enriched solution and micro-bubble dispersion in accordance with the present invention.

As stated earlier, the two-phase micro-bubble containing oxygenated mixture 10 can be used in any application in which oxygen is beneficial, including the treatment of skin wounds and burns. In one application, a skin wound may be submerged in the oxygenated mixture to non-surgically remove dead, devitalized, contaminated and foreign matter from tissue cells. Referring now to FIG. 3, a method for using the two-phase oxygenated mixture 10 in a bath 100 is illustrated. Water having a desired temperature is pumped through an oxygenation system 30. More specifically, the water is conveyed through a pre-charge pump 32 to pressurize the water. Preferably, the pressure of the stream is between 35 psig to 120 psig. In addition, the water preferably has a temperature no greater than 65° F., as warmer temperatures decrease the solubility of the gas in solution and may not be appropriate for the medical condition being treated. The water is discharged from the pre-charge pump 32 and conveyed to the oxygenation system 30 through an influent line 40, which is maintained at low pressure. Oxygen-containing gas is introduced into the influent line 40 from a supply of gas. In FIG. 3, oxygen gas is shown being injected into the liquid stream through a nozzle 50. The gas is injected substantially countercurrent to the flow direction in the influent line 40 at a high velocity. Countercurrent injection of the gas facilitates more complete mixing of the gas in solution, as a result of the instability of the jet plume. Injecting the gas at relatively high pressures further enhances mixing. Preferably, the gas is injected into the influent line 40 at a pressure between 150 psig and 450 psig.

Generation of micro-bubbles in the liquid stream requires a significant amount of energy. As a result, the gas must be introduced at a very high speed into the liquid. In the present method, the gas is preferably introduced at supersonic conditions at the exit of the nozzle 50. The nozzle 50 may be any type of nozzle that permits supersonic gas flow conditions, such as the nozzle disclosed in U.S. Pat. No. 5,463,176. The velocity of the gas at the exit of the nozzle 50 is preferably in the range of Mach 1 to Mach 5 and more preferably in the range of Mach 2 to Mach 4. It will be understood that lesser velocities, such as those below Mach 1, can be used but ordinarily will not provide as much mixing of gas into solution.

The introduction of gas at supersonic conditions into the low-pressure stream creates a two-phase oxygenated mixture 10. The mixture 10 is conveyed through a turbine based pump known as a co-compressor 70, which concurrently increases the pressure of both the gas and liquid in the stream and discharges the mixture into a high-pressure discharge line 75. The pressure of the gas and liquid are increased to allow large quantities of oxygen to efficiently dissolve in the liquid in a short period of time. The elevated pressure also substantially limits the remaining gas micro-bubbles from increasing in size. The amount of pressure in the discharge line 75 varies depending on the size of the system and desired discharge conditions. Preferably, the pressure of the mixture as it enters the discharge line 75 is between 150 and 800 psig. The high-pressure stream is conveyed to a discharge spigot 90 where it is discharged into a bath 100. Alternatively, depending on the pressure head in the high-pressure stream, the stream may be conveyed through a pressure reducer 80 prior to being conveyed to the discharge spigot 90, as shown in FIG. 3. The dissolved oxygen content in the mixture 10 at the point of discharge can be as high as 200 mg/l.

As the mixture 10 is discharged into the bath 100, the tank is allowed to fill with minimal agitation or stirring so as to substantially minimize the amount of nucleation and ebullition of gas bubbles. In this way, the high dissolved oxygen concentration in the mixture 10 may be substantially preserved. Preferably, the bath is filled so that the dissolved oxygen concentration is kept above 20 mg/l at 1 atm and 65° F. Once the bath 100 is filled, the oxygenation system 30 and spigot 90 are turned off, and the patient or the patient's wounded areas are carefully placed in the bath. The solution is allowed to enter tiny fissures or cavities in the wounded tissue. Some of the dissolved oxygen contacts the wounded tissue and aids in the regeneration of new tissue cells. As the solution is circulated in the tissue layers, the dissolved oxygen nucleates into fine micro-bubbles that attach to skin fragments. These micro-bubbles exfoliate damaged tissue layers and carry them to the surface of the bath, assisting in debridement and regeneration of new tissue cells.

Although the elevated dissolved oxygen content in the bath 100 is not stable under atmospheric conditions, in the absence of bubble nucleation, the rate of oxygen liberation at the liquid/atmosphere interface is slow enough that the dissolved oxygen content in the bath can remain elevated for several hours. After this time, the dissolved oxygen content will decrease down to equilibrium conditions. Preferably, ambient pressure at the location of the bath is maintained between 0.9 atm and 1.1 atm.

Energy may be added to the bath solution after the bath is filled to stimulate the nucleation of micro-bubbles and accelerate the exfoliation process. For instance, heat energy may be added to promote homogeneous nucleation. Mechanical mixing or circulation of the bath solution using stirring bars, circulation pumps or other mechanical devices may also stimulate nucleation of micro-bubbles. In FIG. 3, a circulation pump 110 is shown which gently draws solution from the bath and recirculates solution into the bath. In some cases, heat dissipation from the submerged tissue may be sufficient to promote nucleation of micro-bubbles in the proximity of the tissue. Moreover, the addition of solid surfaces in the bath may be used to stimulate heterogeneous nucleation of micro-bubbles.

Figure 4:
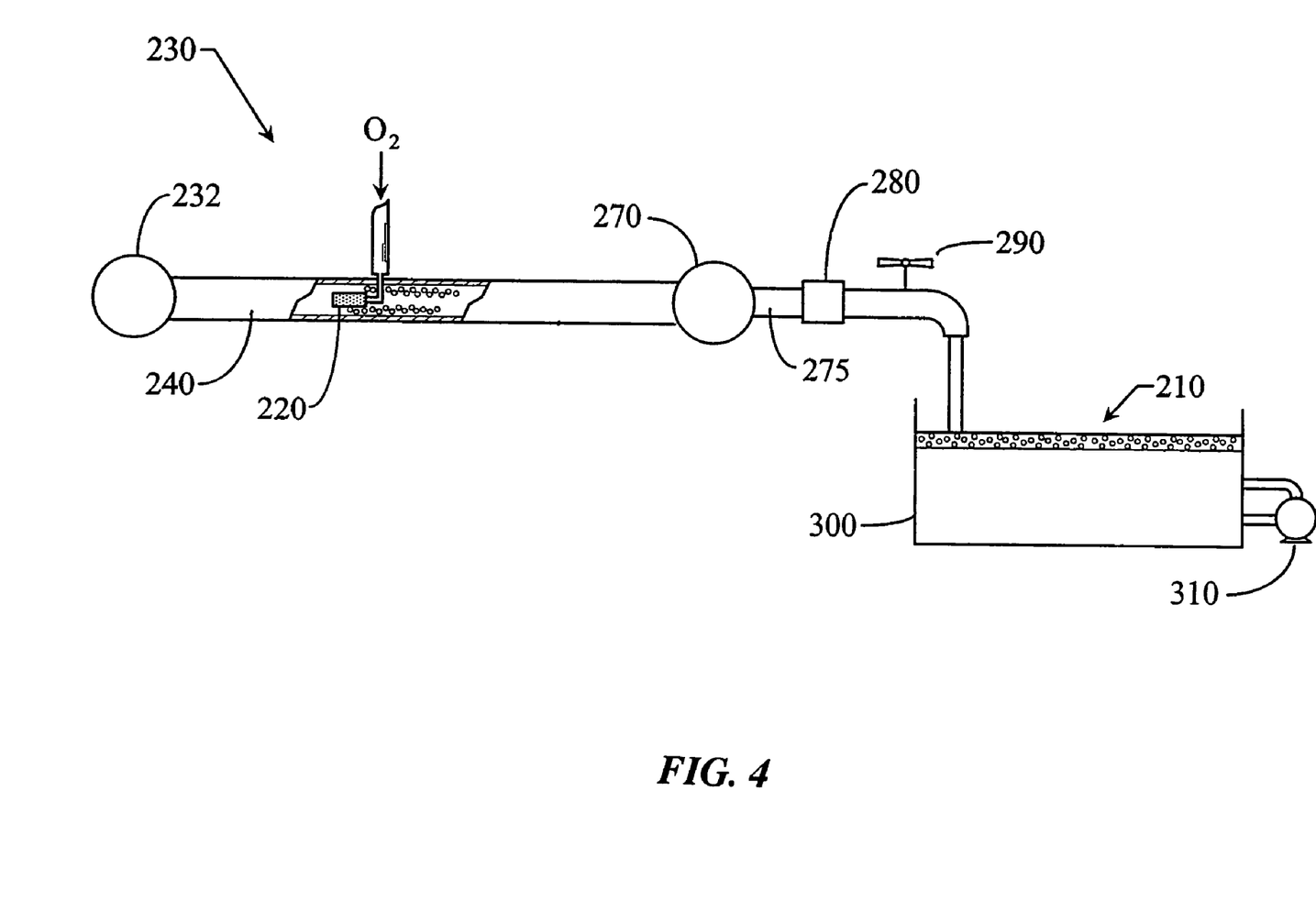
FIG. 4 is a flow chart showing steps of an alternate method for generating and using a gas-enriched solution and micro-bubble dispersion in accordance with the present invention.

As an alternative to high velocity injection through nozzles, porous gas diffusion devices, such as sintered metal diffusers available from Mott Metallurgical, Inc., can be used to introduce gas into the liquid. Referring now to FIG. 4, an alternate method for making a two-phase oxygenated mixture 210 is illustrated. In general, components that are similar or identical to components in FIG. 3 are identified by the same reference number plus 200. Water having a desired temperature is pumped through an oxygenation system 230. The water is conveyed through a pre-charge pump 232 to pressurize the water. Preferably, the pressure of the stream is between 35 psig to 120 psig. In addition, the water preferably has a temperature no greater than 65° F., as warmer temperatures decrease the solubility of the gas in solution and may not be appropriate for the medical condition being treated. The water is discharged from the pre-charge pump 232 and conveyed to the oxygenation system 230 through an influent line 240, which is maintained at low pressure. Oxygen-containing gas is introduced into the influent line 240 through a porous diffusion device 220 connected to a supply of oxygen gas. The diffusion device 220 may have various geometries and be placed in a variety of ways in contact with the liquid. In FIG. 4, a cylindrical diffusion device 220 is shown disposed inside the influent line 240. Gas is delivered through the diffusion device 220 and into the pressurized liquid through a plurality of pores disposed through a the cylindrical face of the diffusion device. Preferably, the pores are no larger than 2 microns in diameter to facilitate the formation of small bubbles of the gas. The pressurized liquid flows past the diffusion device 220 in a direction transverse to the axis of the pores on the diffusion device 220 to create shear stresses along the outlets of the pores. As such, the shear stresses overcome attachment forces and surface tension that hold the micro-bubbles on the diffuser to detach and transport micro-bubbles as soon as they are formed on the diffuser face. In this way, the coalescence of large bubbles on the surface of the diffuser 220 is minimized.

The terms and expressions, which have been employed herein, are used as terms of description and not of limitation. There is no intention in use of such terms and expressions of excluding any equivalents of the features shown and described or portions thereof. It is recognized that various modifications of the embodiments described herein are possible within the scope and spirit of the invention. While the two-phase oxygenated mixture has been described primarily in terms of its use in skin products and topical treatment, the invention is intended for use in any application where a supply of oxygen is desired. For example, the oxygenated solution may be used to enhance tumor treatment or as an oxygen-enriched blood substitute. In the former case, oxygen may increase the chemo-sensitivity or radio-sensitivity of tumor cells, allowing a malignant condition to be more amenable to treatment. As a blood substitute, the oxygen-enriched solution can be administered intravenously in situations where whole blood products are not required. An example of such use is in response to blood loss due to hemorrhage, where fluid and oxygen are in critical need.

The invention is further intended to encompass a wide range of solutes and solvents other than oxygen and water. For instance, injecting nitrogen gas into a solvent can form a two-phase mixture in accord with the present invention. When using the solution for skin debridement, a variety of gases may be dissolved into solution for safely debriding the tissue. A bath solution may be prepared using one or more gases, including, but not limited to air, carbon dioxide or a number of inert gases. Gas may be dissolved into or even reacted with a number of different solvents, such as propylene glycol or perflubrons to form a two-phase mixture. Accordingly, the present invention is not limited to the specific embodiments discussed above, but rather incorporates variations that fall within the scope of the following claims.

The invention claimed is:

1. A gas-containing mixture, comprising:
   a solution of oxygen gas dissolved in water and a thickening agent, the concentration of dissolved oxygen in said solution being greater than 20 m/l at 1 atm and 65°;
   and a plurality of micro-bubbles of the gas, said micro-bubbles each exerting a buoyancy force;
   said mixture having a yield stress greater than the buoyancy force exerted by the micro-bubbles and being effective to immobilize the microbubbles in a stable dispersion under atmospheric pressure and static conditions.

2. The mixture of claim 1, wherein the average diameter of the micro-bubbles is between 10-200 microns.

3. The mixture of claim 1, wherein the average diameter of the micro-bubbles is between 10 and 80 microns.

4. The mixture of claim 1, wherein the thickening agent is a polymer-based thickening agent.

5. The mixture of claim 1, wherein the thickening agent is a clay-based thickening agent.

6. A composition of matter in the form of an oxygen-in-liquid dispersion comprising, as a continuous phase, a mixture of water a thickening agent, and dissolved oxygen, the concentration of dissolved oxygen in said continuous phase being greater than 20 mg/l at 1 atm and 65°F, and, as a disperse phases oxygen micro-bubbles which are dispersed in and exert a buoyancy force on said continuous phase; and said continuous phase being characterized by the following equation:

$$\tau = +/- \tau_o + \eta_p \gamma$$

where
- $\tau$ is sheer stress,
- $\tau_o$ is yield stress,
- $\eta_p$ is plastic velocity viscosity and
- $\gamma$ is strain rate the yield stress of said continuous phase being greater than the buoyancy force exerted by said micro-bubbles, said being effective to stabilize said gas micro-bubbles in said composition in a static condition, thereby inhibiting release of said gas from said composition.

* * * * *